United States Patent [19]

Zinnes et al.

[11] 4,013,686
[45] Mar. 22, 1977

[54] 4-(1-PYRROLIDINYL)-2H-1-BENZOTHIO-PYRAN-1,1-DIOXIDE

[75] Inventors: Harold Zinnes, Rockaway; Neil A. Lindo, Chatham, both of N.J.

[73] Assignee: Warner-Lambert Company, Morris Plains, N.J.

[22] Filed: Dec. 6, 1974

[21] Appl. No.: 530,254

Related U.S. Application Data

[60] Division of Ser. No. 421,556, Dec. 4, 1973, abandoned, which is a division of Ser. No. 243,523, April 7, 1972, abandoned, which is a continuation-in-part of Ser. No. 163,076, July 15, 1971, abandoned.

[52] U.S. Cl. .................. 260/326.84; 260/247.1 P; 260/293.57; 260/327 TH; 424/275
[51] Int. Cl.² .................................. C07D 409/04
[58] Field of Search ... 260/327 R, 326.35, 247.1 P, 260/293.57, 326.84, 327 TH, 562 K

[56] References Cited

UNITED STATES PATENTS

| | | | |
|---|---|---|---|
| 2,610,183 | 9/1952 | McKellin et al. | 260/247.1 P |
| 3,636,049 | 1/1972 | McManus | 260/327 TH |
| 3,639,614 | 2/1972 | Rosen et al. | 260/327 R |

OTHER PUBLICATIONS

Boisser et al., Chemical Abstracts, vol. 74 (1971), 111,911v.
Chemical Abstracts, 8th Collective Index, (1967–1971), p. 4529s.

*Primary Examiner*—Paul M. Coughlan, Jr.
*Attorney, Agent, or Firm*—Albert H. Graddis; Frank S. Chow; George M. Yahwak

[57] ABSTRACT

Processes for the production of the compounds of the formula:

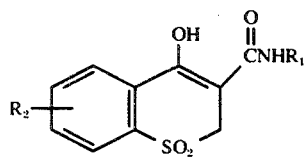

are disclosed.

In the above formula, $R_1$ is aryl which may be substituted or unsubstituted; $R_2$ is hydrogen, alkyl, aryl, aralkyl, alkoxy, halogen, cyano, nitro, trifluoromethyl and the like.

These compounds are prepared by the following reaction schemes:

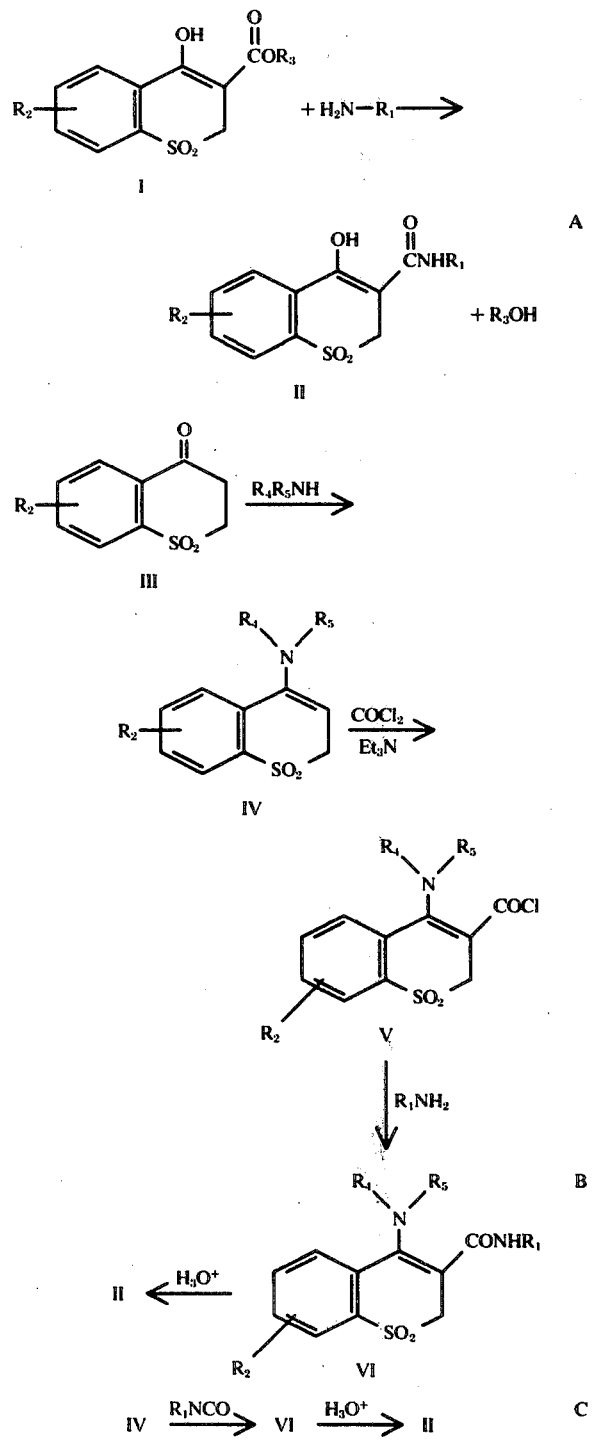

These compounds are useful as anti-inflammatory agents.

1 Claim, No Drawings

4-(1-PYRROLIDINYL)-2H-1-BENZOTHIOPYRAN-1,1-DIOXIDE

This is a division of application Ser. No. 421,556 filed Dec. 4, 1973 which in turn is a divisional of Ser. No. 243,523, filed Apr. 7, 1972 which in turn is a continuation-in-part of Ser. No. 163,076, filed July 15, 1971, all now abandoned.

The present invention is concerned with novel processes for the production of 4-hydroxy-2-H-1-benzothiopyran-3-carboxamide 1,1-dioxides having the following structural formula:

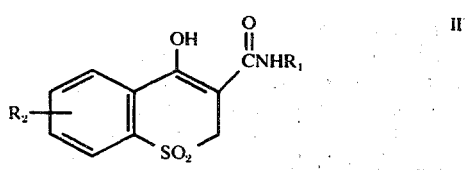

wherein $R_1$ is aryl which may be substituted or unsubstituted; $R_2$ is hydrogen, alkyl, aryl, aralkyl, alkoxy, halogen, cyano, nitro, trifluoromethyl and the like.

The above compounds as disclosed in U.S. Ser. No. 163,076 are useful as anti-inflammatory agents. For example, when they are administered orally or intraperitoneally to laboratory animals such as rats at a dose of 10–200 mg/kg, they are capable of reducing the swelling in their paws induced by the injection of an irritant such as carrageenin. According to the present invention new and commercially feasible processes are provided for the production of these compounds.

The first process consists in aminolysis of a β-keto-ester of Structure I. This is best carried out by refluxing compound I with the appropriate amine in an inert solvent such as xylene in the presence of molecular sieve. The latter serves to remove the alcohol which is formed in the reaction. This reaction may be represented by the following reaction scheme:

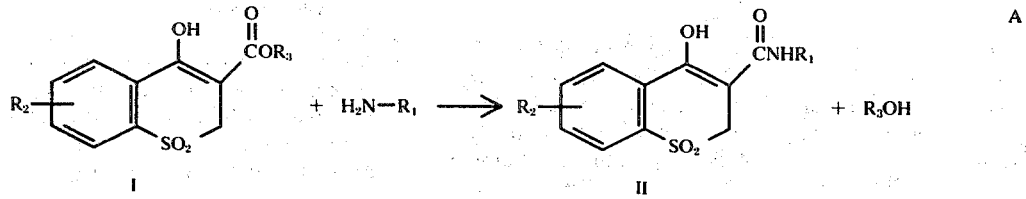

wherein $R_3$ is alkyl or aryl.

The second process starts with the conversion of a thiochroman-4-one 1,1-dioxide of Structure III to an enamine of Structure IV by reaction with a secondary amine of Structure $R_4R_5NH$ where $R_4$ and $R_5$ are alkyl or where $R_4$ and $R_5$ are joined together to form a heterocyclic ring such as pyrrolidine, piperidine, or morpholine. This is then reacted with phosgene and triethylamine to give the acid chloride V. Treatment of the latter with an appropriate amine in the presence of triethylamine gives rise to the enamine-amide VI. Acid hydrolysis, e.g., with an aqueous acid, of VI gives the target compound II. The process can be carried out without actually isolating V or VI. This reaction is illustrated in the following reaction scheme:

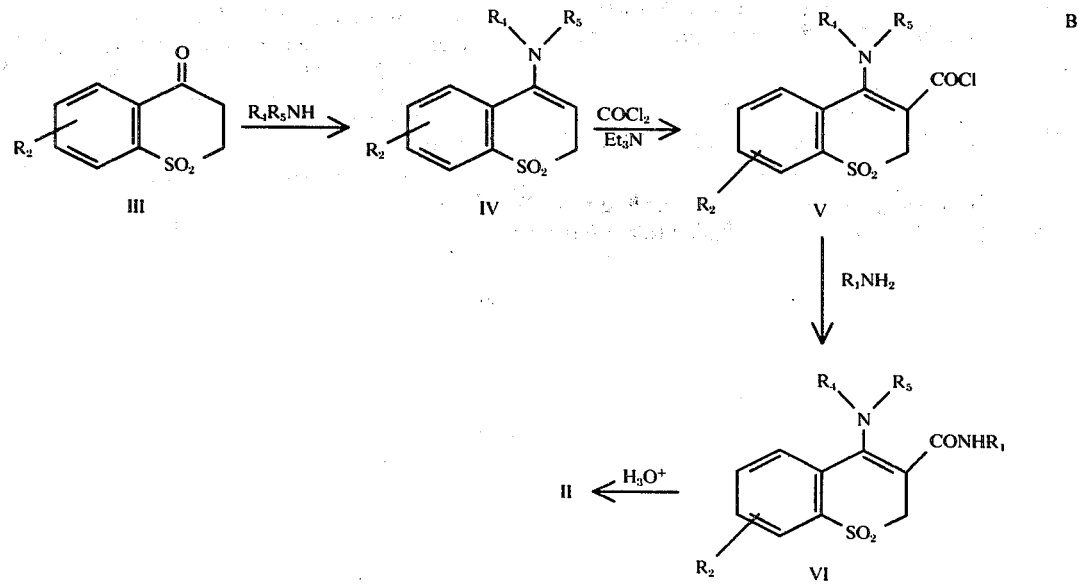

In the third process, enamine IV is heated with an isocyanate of Structure $R_1NCO$. The isocyanate, which is used in excess, serves as the solvent for the reaction. This reaction gives rise to VI which can be hydrolyzed to II. As in the second process, VI is not isolated as such but is hydrolyzed directly to II. This reaction is represented by the following reaction scheme:

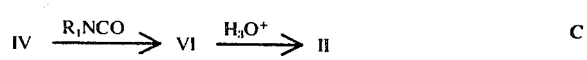

Starting materials I and II above are prepared in accordance with the description by W. J. Still, et al., J.O.C., 33, 2730 (1968).

In order to further illustrate the practice of this invention, the following examples are included:

EXAMPLE 1

4-Hydroxy-2H-1-benzothiopyran-3-carboxanilide 1,1-Dioxide.

Preparation by Aminolysis of the β-Ketoester. — A mixture of 11.7 g. (0.05 mole) of methyl 4-hydroxy-2H-1-benzothiopyran-3-carboxylate 1,1-dioxide, 7.0 g. (0.075 mole) of aniline, and 250 ml. of xylene was refluxed for 16 hr. in a Soxhlet apparatus, the thimble of which contained 20 g. of Linde type 4A molecular sieve. The mixture was cooled and the resulting precipitate was collected to give 12.8 g. (81%) of product, m.p. 204°–208° dec. Recrystallization from ethyl acetate gave 11.4 g. material, m.p. 205°–208° dec.

Anal. Calcd for $C_{16}H_{13}NO_4S$: C, 60.94; H, 4.16; N, 4.44; S, 10.17. Found: C, 60.84; H, 4.25; N, 4.20; S, 10.15.

EXAMPLE 2

4-(1-Pyrrolidinyl)-2H-1-benzothiopyran 1,1-Dioxide.

A mixture of 9.8 g. (0.05 mole) of thiochroman-4-one 1,1-dioxide, 5.3 g. (0.075 mole) of pyrrolidine, and 150 ml. of benzene was placed in a flask equipped with a Dean-Stark water separator and was refluxed for 4 hr. The precipitate (4.9 g.) which separated on standing at room temperature was collected. Concentration to one-fourth the original volume gave an additional 5.0 g. These crops were combined and recrystallized from benzene to give 8.0 g. of product, m.p. 154°–157° dec.

EXAMPLE 3

4-Hydroxy-2H-1-benzothiopyran-3-carboxanilide 1,1-Dioxide.

Preparation from the enamine-acid chloride. — To 28.5 g. of a 12.5% solution of phosgene in benzene was added 30 ml. of tetrahydrofuran. The temperature of the solution was maintained at −10° to −15° and a solution of 7.5 g. (0.03 mole) of 4-(1-pyrrolidinyl)-2H-1-benzothiopyran 1,1-dioxide and 5 ml. (0.036 mole) of triethylamine in 125 ml. of tetrahydrofuran was added with stirring over a period of 20 minutes. After stirring at room temperature for 2 hr., a solution of 3.1 g. (0.033 mole) of aniline and 5 ml. of triethylamine in 25 ml. of tetrahydrofura was added, the mixture was refluxed for 2 hr., and about a third of the solvent was distilled off. The remaining mixture was poured into ice-water and extracted with dichloromethane. The organic layer washed well with water, dried ($MgSO_4$) and evaporated to give 12.3 g. of a dark syrup. This crude enamine-amide was dissolved in 100 ml. of methanol, treated successively with 10 ml. of water and 2 ml. of concentrated hydrochloric acid, and heated on a steam bath for 20 minutes. The mixture was cooled and filtered to yield 6 g. (64%) of product, m.p. 204°–208°.

EXAMPLE 4

4-Hydroxy-2H-1-benzothiopyran-3-carboxanilide 1,1-Dioxide.

Preparation by Reaction of the Enamine with Phenylisocyanate. — A mixture of 2.5 g. of 4-(1-pyrrolidinyl)-2H-1-benzothiopyran 1,1-dioxide and 5 ml. of phenylisocyanate was heated to boiling and then heated on a steam bath for 10 minutes. The resulting dark oil was diluted with 50 ml. of methanol, treated successively with 10 ml. of water and 2 ml. of concentrated hydrochloric acid, and heated on a steam bath for 20 minutes. The reaction mixture was poured into water, extracted with dichloromethane and the organic layer was extracted with 1N sodium hydroxide. Acidification of the alkaline solution resulted in the precipitation of 2.0 g. (63%) of crystalline material. Recrystallization from methanol gave 1.1 g. of pure product, m.p. 205°–208°.

We claim:
1. 4-(1-pyrrolidinyl)-2H-1-benzothiopyran-1,1-dioxide.

* * * * *